(12) United States Patent
Moskovich et al.

(10) Patent No.: US 9,980,798 B2
(45) Date of Patent: May 29, 2018

(54) PACKAGED ORAL CARE IMPLEMENT (71) Applicant: COLGATE-PALMOLIVE COMPANY, New York, NY (US)

(72) Inventors: Robert Moskovich, East Brunswick, NJ (US); Marisela Hernandez, New York, NY (US); Paul Donald Carse, Milford, NJ (US); Mathew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 96 days.

(21) Appl. No.: 14/364,948

(22) PCT Filed: Dec. 14, 2012

(86) PCT No.: PCT/US2012/069627
§ 371 (c)(1),
(2) Date: Jun. 12, 2014

(87) PCT Pub. No.: WO2013/090659
PCT Pub. Date: Jun. 20, 2013

(65) Prior Publication Data
US 2014/0339111 A1    Nov. 20, 2014

Related U.S. Application Data (60) Provisional application No. 61/576,652, filed on Dec. 16, 2011.

(51) Int. Cl.
B65D 83/10    (2006.01)
A61C 19/02    (2006.01)
(Continued)

(52) U.S. Cl.
CPC ............ A61C 19/02 (2013.01); B65D 75/324 (2013.01); B65D 75/326 (2013.01);
(Continued)

(58) Field of Classification Search
CPC .. A45D 44/18; A45K 1/09; A46B 2200/1066; A61C 19/006; A61C 15/04;
(Continued)

(56) References Cited

U.S. PATENT DOCUMENTS 5,791,478 A    8/1998  Kalvelage et al.
6,279,736 B1 *  8/2001  Hekal ................ B01J 20/28019
                                                          206/204
(Continued)

FOREIGN PATENT DOCUMENTS

CN    1419511    5/2003
CN    2790947    6/2006
(Continued)

OTHER PUBLICATIONS

Corresponding Chinese Office Action dated Nov. 11, 2015.
(Continued)

*Primary Examiner* — J. Gregory Pickett
*Assistant Examiner* — Rafael Ortiz (57) ABSTRACT A package (11) that comprises a front cover (40) and a back cover (60), at least a first portion of the front cover (40) or the back cover (60) being formed of a first material, and one of the front cover (40) and the back cover (60) being formed of a second material, the second material being more rigid than the first material. The first portion formed of the first material is capable of being deflected without permanent deformation of the display package. An oral care implement (10) may be included within the package (11) and in some embodiments, the first portion is adjacent the head (27).

18 Claims, 5 Drawing Sheets (51) Int. Cl.
*B65D 75/36* (2006.01)
*B65D 75/32* (2006.01)
*A46B 9/04* (2006.01)

(52) U.S. Cl.
CPC .............. *B65D 75/366* (2013.01); *A46B 9/04* (2013.01); *B65D 2201/00* (2013.01); *B65D 2575/3245* (2013.01)

(58) Field of Classification Search
CPC ...... A61C 19/02; B65D 75/30; B65D 75/326; B65D 75/366; B65D 75/324
USPC ......... 206/361, 362, 362.1, 362.2, 363, 368, 206/369, 769, 205, 207, 209, 209.1, 349, 206/531, 524.1, 524.3, 524.4, 524.6; 15/22.1
See application file for complete search history.

(56) References Cited

U.S. PATENT DOCUMENTS

| | | | |
|---|---|---|---|
| 6,954,961 B2 | 10/2005 | Ferber et al. | |
| 7,094,981 B2* | 8/2006 | Sorrentino | A61C 17/221 15/22.1 |
| 7,143,462 B2 | 12/2006 | Hohlbein | |
| 2003/0205492 A1 | 11/2003 | Ferber et al. | |
| 2005/0087464 A1 | 4/2005 | Brattesani et al. | |
| 2005/0145519 A1* | 7/2005 | Fattori | B65D 25/20 206/361 |
| 2005/0161313 A1 | 7/2005 | Sorrentino et al. | |
| 2009/0090643 A1 | 4/2009 | Fischer et al. | |
| 2009/0194451 A1* | 8/2009 | Leiner | B65D 75/327 206/524.1 |
| 2011/0036736 A1* | 2/2011 | Knowlton | A61B 19/026 206/438 |

FOREIGN PATENT DOCUMENTS

| | | |
|---|---|---|
| GB | 1584392 | 2/1981 |
| WO | WO2005082268 | 9/2005 |
| WO | WO2009/116997 | 9/2009 |

OTHER PUBLICATIONS

Corresponding Chinese Search Report dated Nov. 11, 2015.
International Search Report and the Written Opinion issued in International Application PCT/US2012/69626 dated Jun. 7, 2013. WO.
Written Opinion of the International Preliminary Examining Authority issued in International Application PCT/US2012/69626 dated Feb. 7, 2014. WO.

* cited by examiner

PACKAGED ORAL CARE IMPLEMENT

CROSS-REFERENCE TO RELATED PATENT APPLICATIONS

The present application is a U.S. national stage entry under 35 U.S.C. § 371 of Patent Cooperation Treaty Patent Application No. PCT/US2012/69627, filed Dec. 14, 2012, which claims priority to U.S. Provisional Application No. 61/576,652, filed Dec. 16, 2011, the entirety of which is incorporated herein by reference.

FIELD OF THE INVENTION

The present invention relates to packaging, and more specifically to packaging of oral care implements.

BACKGROUND OF THE INVENTION

One common type of display packaging for an oral care implement, such as a toothbrush, comprises blister packaging that includes a rigid, transparent front cover made of a clear plastic film that permits visual inspection of the oral care implement.

The quality and functional characteristics of oral care implements can vary greatly. Providing consumers with all of the information needed to make optimal purchasing decisions at the point of sale can be challenging due to the relatively small size of the packages, and due to the need to keep the oral care implement enclosed in the package. There is a need for improved display packaging to help consumers make mote informed purchasing decisions

BRIEF SUMMARY OF THE INVENTION

Some packages in accordance with embodiments of the invention address the above problems while providing, a cover to keep the packaged implement clean, and also providing sufficient mechanical strength and durability to withstand the static and dynamic loads associated with transporting the toothbrushes from factory to market without rupture or disfigurement of the packaging or the toothbrushes. In particular, it is desirable that the bristles be protected from exposure to prolonged loads that might permanently bend them or otherwise alter their configuration in a way that would impair them functionally or aesthetically.

In one embodiment, the invention can comprise a package comprising a front cover and a back cover, at least a first portion of the front cover or the back cover being formed of a first material, and one of the front cover and the back cover being formed of a second material, the second material being more rigid than the first material. The first portion formed of the first material is capable of being deflected without permanent deformation of the package.

In another embodiment, the invention can comprise a packaged oral care implement comprising an oral care implement having a plurality of tooth engaging elements and a handle, a blister package having a front and back cover enclosing the oral care implement, the front cover including a flexible region, and the flexible region having an original configuration in which the flexible region is disposed adjacent to the tooth engaging elements. The flexible region is made of a first material and other regions of the package are made of a second material that is different from the first material, and the first material being more flexible than the second material.

In yet another embodiment, the invention can comprise a packaged oral care implement comprising an oral care implement having at least one flexible element, and a package enclosing the oral care implement. The package including at least one rigid region and a flexible region adjacent the at least one flexible element of the oral care implement. The flexible region being made of a material having a first modulus of elasticity ($\lambda_1$), and the at least one of the rigid region being made of a material having a second modulus of elasticity ($\lambda_2$), wherein ($\lambda_1$)/($\lambda_2$)<1.

Some packages of the types described herein can be manufactured inexpensively using techniques in which the film is formed into a blister shape using a thermoforming process in which the film is heated, and pressure/vacuum forms the heated film into a shape dictated by a mold. The resulting blister shape then is cut and assembled to the back cover by using fastening techniques such as sealing/welding.

The packaged oral care implement has the advantage of allowing consumers to better engage with the product prior to making a purchasing decision, and allows consumers to customize the degree of engagement.

The packaged oral care implement further provides the advantage of a package which maintains its general configuration even after tactile engagement by multiple consumers, thus reducing the number of on-display products which have unsightly packaging. The packaged oral care implement also has the advantage of reducing the number of packages which are no longer suitable for sale due to consumer engagement with the product prior to purchase.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above" "below," "up" "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated, as such. Terms such as "attached," "affixed," "connected," "coupled," "interconnected," and similar terms refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 1:
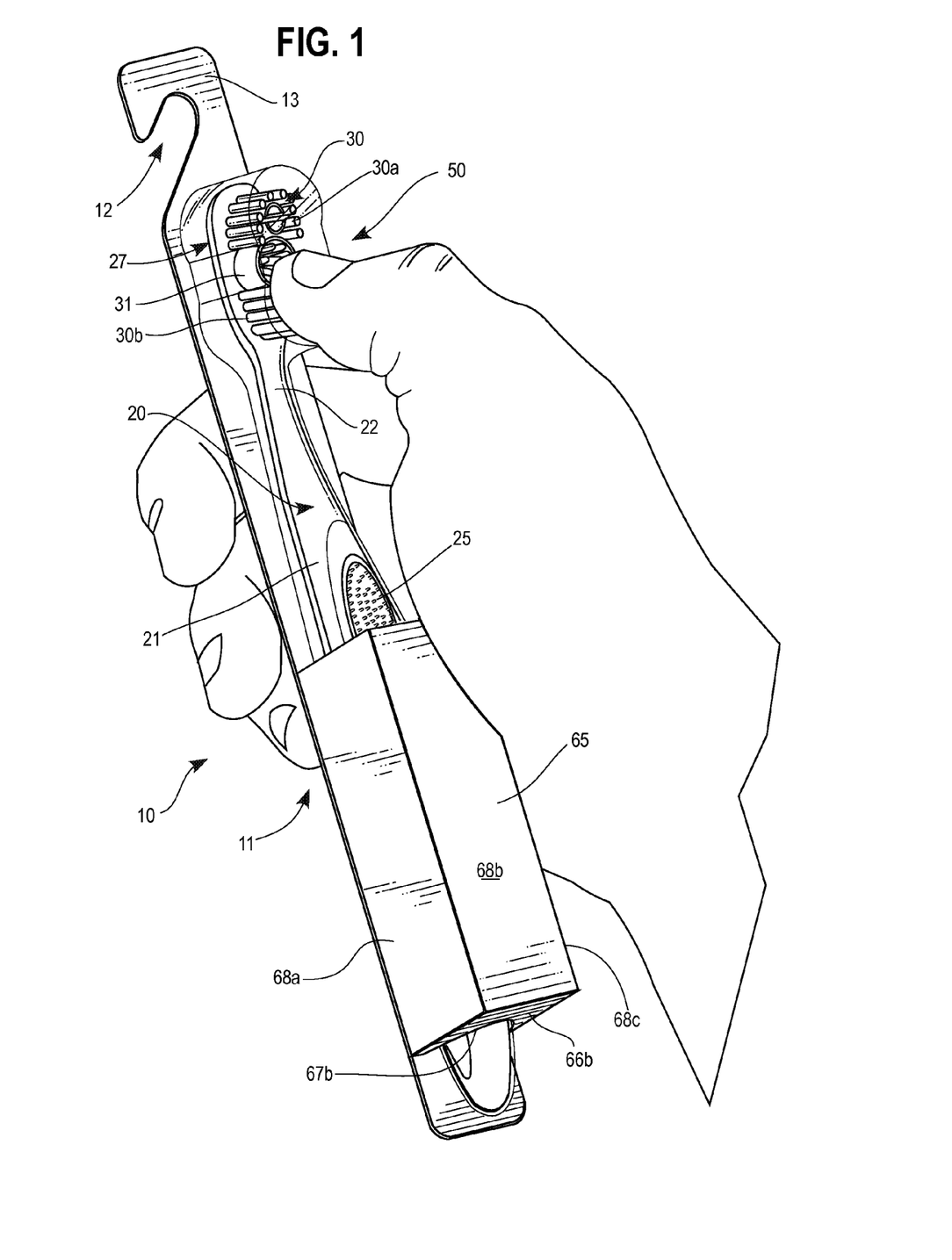
FIG. 1 is a perspective view of a user engaging with a package constructed accordion to a first embodiment of the present invention.
Figure 2:
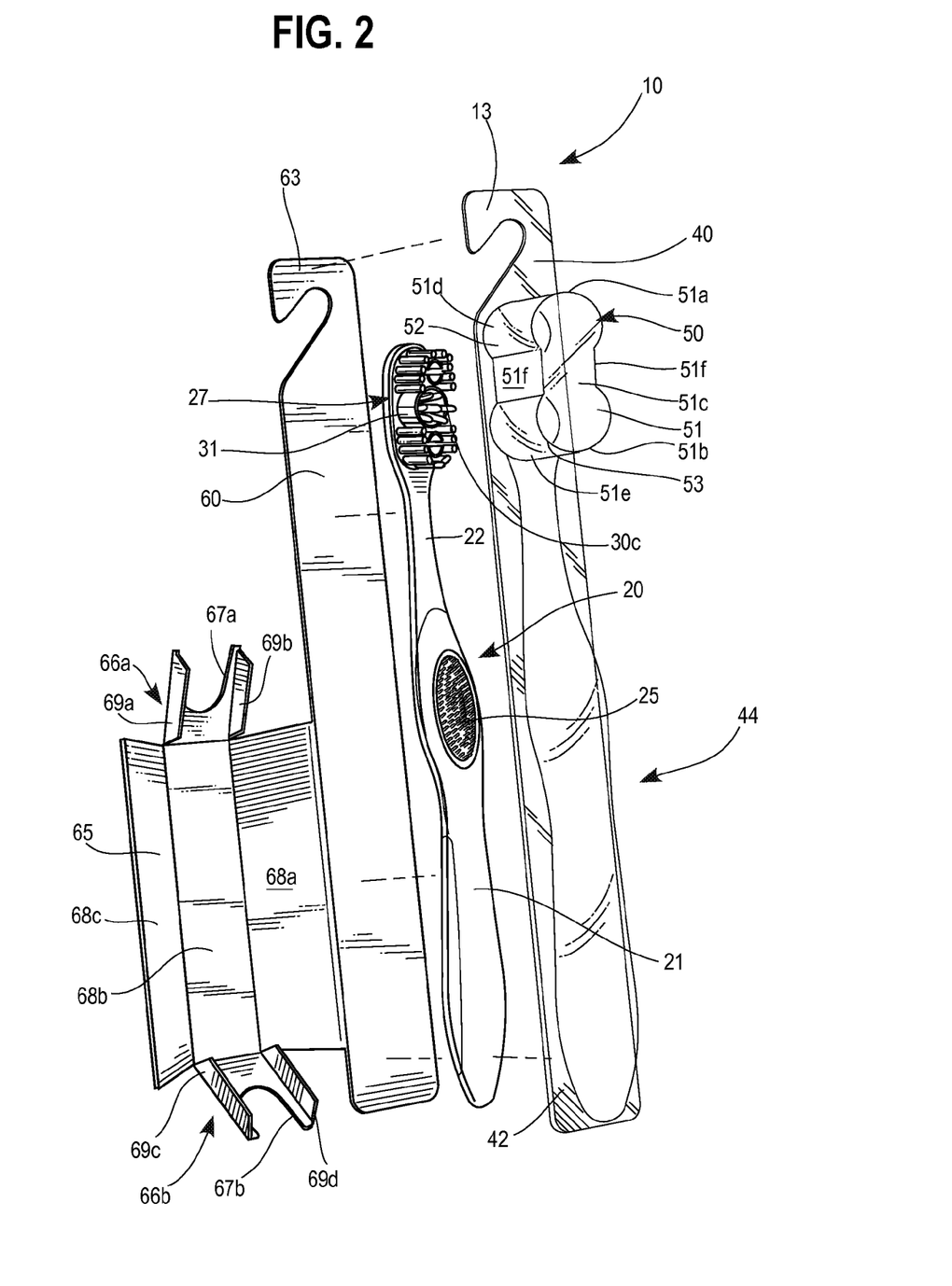
FIG. 2 is an exploded perspective view of the package of FIG. 1.

FIGS. 1-2 illustrate a packaged oral care implement 10 that includes a toothbrush 20 and a display package 11. The display package 11 comprises a front cover 40 and a back cover 60 to which the front cover is mounted to enclose the toothbrush 20. In the embodiment as shown, the packaged oral care implement 10 is a manual toothbrush 20. However, in other embodiments, other types of toothbrushes, including both manual and electric toothbrushes, as well as other types of oral care implements, including tongue cleaners, tooth polishers, oral care material dispensers, and other oral care implements, may be employed to provide a packaged oral care implement as described herein.

The illustrated toothbrush 20 comprises a head 27, a neck 22, and a handle 21. The handle 21 provides the user with a mechanism to readily grip and manipulate the toothbrush 20. If desired, the handle 21 may include a suitable textured grip made of soft elastomeric material. The handle 21 can be of single or multi-part construction. Suitable textured grips for the handle 21 can comprise grip zones or pads 25, 24 disposed on the front and back of the handle 21 respectively. The handle 21 may also be contoured and/or angled to provide an ergonomic grip. To further enhance the handling characteristics, and specifically to make the handle more easily gripped, particularly when wet, the handle 21 may further comprise a surface treatment such as a pattern of raised ribs 26 (referring to FIG. 3) on the back of the handle 21 near its proximal end.

The handle 21 transitions into the neck 22 at its distal end. The neck 22 may or may not have a smaller transverse cross-sectional area than the handle 21. The neck 22 can be considered as a portion of the handle 21, or the head can be considered as being connected to a distal end of the handle 21 via the neck 22. The head 27 may be wider or wider than the neck 22, or may be a continuous extension or narrowing of the handle 21.

Figure 3:
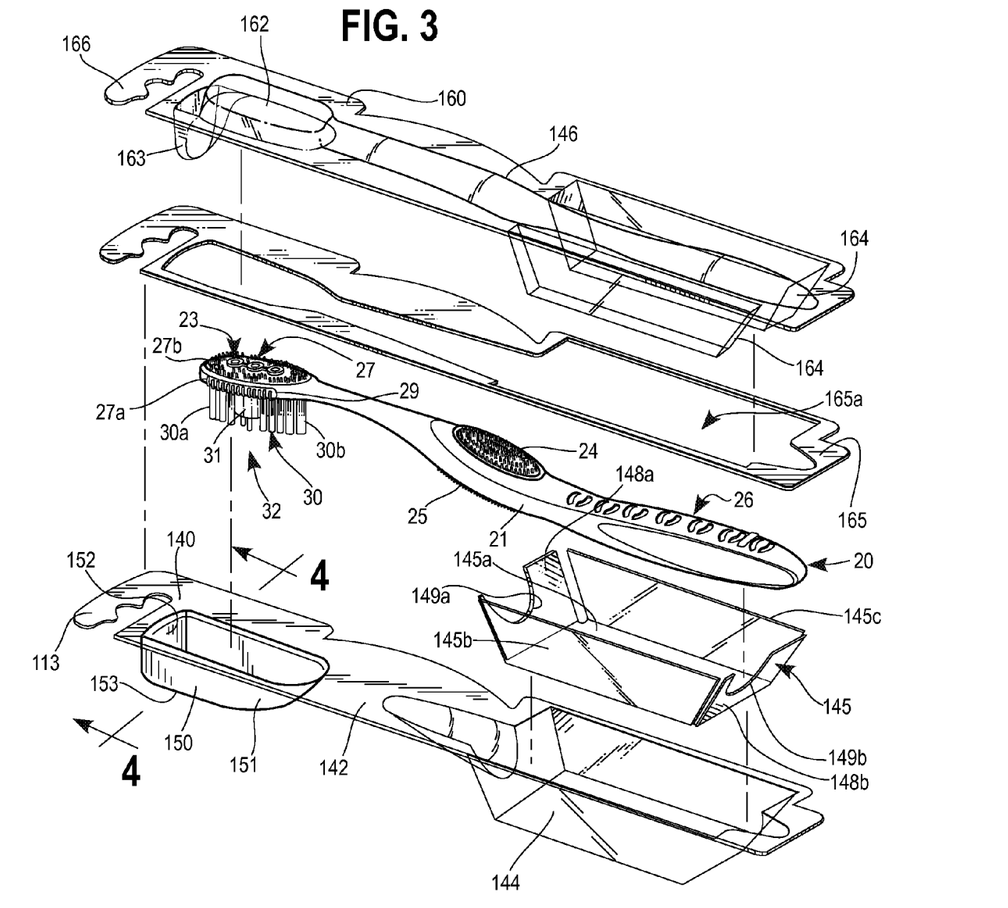
FIG. 3 is an exploded perspective view of a second embodiment.
Figure 5:
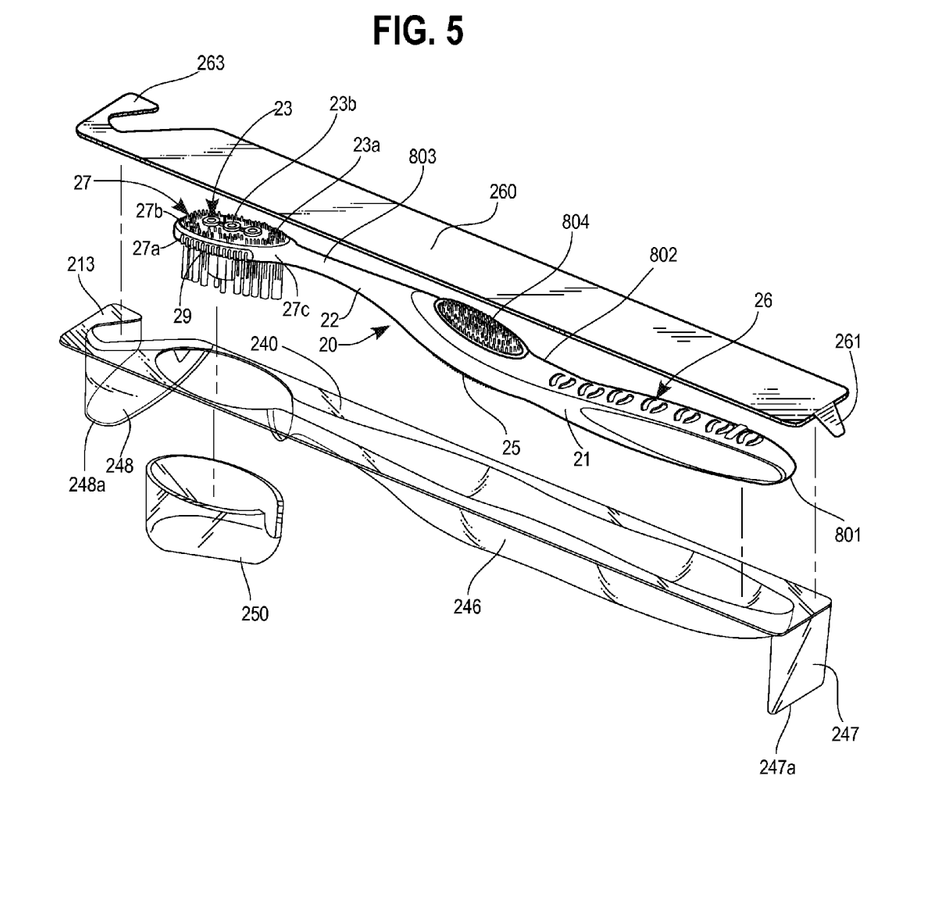
FIG. 5 is an exploded perspective view of a third embodiment.

As shown in FIG. 3, the head 27 generally comprises a front surface 27a, a rear surface 27b, and a peripheral surface 27c. The front surface 27a and the rear surface 27b of the head 27 are opposite one another and call take on a vide variety of shapes and contours. For example, the front and rear surfaces 27a, 27b can be planar, convex, concave, or otherwise contoured, or may include various combinations thereof. The rear surface 27b may comprise a soft tissue cleanser 23, which can be used to cleanse soft tissue of interior portions of the oral cavity such as the tongue and cheeks. The soft tissue cleanser 23 may be made of an elastomeric material, such as a thermoplastic elastomer, and comprises a plurality of protuberances 23a, 23b for engaging and/or massaging soft oral tissue. The protuberances can be any suitable size or shape, or arrangement. As illustrated in FIG. 5, the protuberances may be finger-like projections 23a, or circular projections 23b. Details of another suitable soft tissue cleanser are disclosed in U.S. Pat. No. 7,143,462, issued Dec. 5, 2006 to Colgate-Palmolive Company, which is hereby incorporated by reference.

The front surface 27a of the head 27 comprises a collection of tooth engaging elements 32 extending therefrom for cleaning and/or polishing contact with a user's teeth. While the collection of tooth engaging elements 32 is preferably suited for brushing teeth, the collection of tooth engaging elements 32 can also be used to polish teeth instead of, or in addition to cleaning teeth. As used herein, the term "tooth engaging elements" is used in a generic sense to refer to any structure that can be used to clean, polish, or wipe the teeth through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethyelene/butylene-styrene block copolymer (SEBS) manufactured by GLS Corporation. SEBS material from other manufacturers or other materials within and outside the noted hardness range could also be used.

Further as illustrated, the head 27 comprises tooth engaging elements 32 which include bristles 30, and a polishing cup 31. Bristles 30 can be arranged in upper and lower tuft blocks 30a, 30b, wherein tuft block 30a is arranged above the polishing cup 31, and tuft block 30b is arranged below the polishing cup 31. A central tuft block 30c may be disposed within the polishing cup 31. While the foregoing disclosure describes a particular arrangement of tooth cleaning elements on the head 27, it is understood that the present invention is not so limited to any particular arrangement of the tooth cleaning elements.

Referring back to FIGS. 1-2, the display package 11 may be any type of packaging suitable for display of a packaged oral care implement, such as a blister type package. The display package 11 includes a display engagement region 12 comprising an open-ended diagonal slot as shown. In other embodiments, other display engagement structures may be provided, e.g., closed-ended elongated horizontal slots, circular or oval openings, or the like. The display engagement region 12 is shaped to accommodate various display arrangements such as a display rod, hook or a peg. The display engagement region in the embodiments illustrated in FIGS. 1, 2, 3, and 5 may comprise a front cover display engagement arm 13, 113, or 216 disposed in contact with a corresponding back cover display engagement arm 63, 166, or 263 when the front and back covers are joined together. In other embodiments, the display engagement region 12 may comprise a hanger aperture (not shown) located near a top end of the display package 11 for which the packaged oral care implement may be hung for display in a retail store.

In the embodiment illustrated in FIGS. 1-2, the entire front cover 40 is substantially transparent. In other embodiments, the front cover 40 may be only partially transparent to allow consumers to view portions of the oral care implement 20 from the front of a retail display prior to purchase. As a result, surfaces of the visible portions of the toothbrush 20 can be viewed by the consumer without removing the toothbrush 20 from the display package 11 or compromising the integrity of the package 11. As used herein, the term "transparent" includes materials that allow a user to see through the material, even if the material is colored or includes a degree of translucency.

The front cover 40 includes a cavity 44 that may be three-dimensionally contoured to correspond generally to the shape of the toothbrush 20. The cover may comprise thermoformed plastic films. Suitable thermoformed plastic films may include materials such as polyethylene terephthalate (PET, PETA PETG, PETGAG), polyvinyl chloride (PVC), polypropylene (PP), or styrol-butadiene-block copolymer (SBS), preferred PCV. Other suitable materials for the thermoformed plastic film include, without limitation, renewable primary products, for example of cornstarch, sugar (polyhydroxybutyrate/-valerate), cellulose diacetate, cellulose nitrate, and polylactide (PLA). As illustrated in FIG. 2, the front cover 40 further includes a flange region 42 surrounding the cavity 44. The flange region 42 provides a flat surface for contact with the back cover 60. The flange region 42 may be sealed to the back cover 60 over its entire surface or a portion thereof by heat sealing techniques, pressure-sensitive adhesive, mechanical fasteners such as staples, by wrapping portions of the side edges of the front cover 40 around the back cover 60, and/or by other suitable techniques.

Also as illustrated, the package 11 includes a resilient flexible bubble region 50 on the front cover 40. The flexible bubble region 50 allows a consumer to engage with the oral care implement without permitting direct contact, without permitting the user to physically come into contact with the oral care implement. In some circumstances, a user may desire to engage with the bristles to assess the softness of the bristles; in other instances, a user may desire to palpate the bristles for other reasons. As the transparent cover 40 allows for a visual inspection of the oral care implement, in particular if the toothbrush design further incorporates drawings or other figures attractive to children, children may also desire to engage with the toothbrush by pressing on the bubble region 50 near the toothbrush head 27 or on other regions of the package.

The flexible region 50 is located on the front cover 40 adjacent the bristles 30. In FIG. 2, the flexible region 50 is shown in an original, undeflected configuration. The original undeflected configuration may provide that the flexible region 50 is spaced from the bristles 30, as illustrated in FIG. 1. In other embodiments, the flexible region 50 may be in contact with the bristles 30 in its original, undeflected configuration. The flexible region 50 is sufficiently flexible and resilient to enable bristle stiffness to be assessed by manual palpation and deflection without direct contact and without permanent deformation of the display package 11. The flexible region 50 is made from a material which is sufficiently soft, sufficiently flexible, and sufficiently resilient to permit the soft flexible region to be manually deflected to enable bristle stiffness to be assessed by manual palpation through the soft flexible region 50.

Any suitable material having sufficiently soft, flexible, and resilient characteristics can be used for construction of the flexible region 50. In one embodiment, the material used for construction of the flexible region 50 is thermoplastic polyurethane (TPU). Certain other materials may also be suitable, including, e.g., silicone, synthetic and natural rubbers, elastomers, and monolayer or multilayer films including one or more layers of materials such as polyvinyl alcohol, polymethylmethactylate, polyamide, polycarbonate, polyethylene, polypropylene, polyvinyl chloride, polystyrene, or combinations thereof. It is preferred that the materials not have any tendency to crinkle or crease when subjected to deflection by consumers.

The flexible region or bubble 50 should be sufficiently flexible to allow bending and conformation of the flexible region 50 to a user's thumb or fingers and to allow bending and manipulation of the bristles 30. The flexible region 50 should be sufficiently resilient to withstand multiple deflections of varying magnitudes to deflect the flexible region 50 into contact with portions of the toothbrush 20, and to consistently and reliably revert to its original configuration.

The term "bubble" as used herein refers broadly to a region that can be deflected. In the embodiment shown in FIGS. 1 and 2, the bubble 50 is sized to partially surround the head 27 of the toothbrush 20. The bubble 50 preferably is configured to accommodate repeated cycles of deflection and reversion to its original shape without wrinkling, creasing, or other effects that might detract from its appearance. To this end, the bubble 50 preferably does not have sharp corners. The bubble 50 as shown may be described as generally peanut-shaped, comprising upper and lower lobes 51a and 51b that have generally cylindrical sidewall portions 51d and 51e. Generally planar sidewall portions 51f and top wall portion 51c connect the upper and lower lobes 51a, 51b, and a generally planar front wall 51 adjoins the side wall portions 51d, 51e along an edge 53 which may be well-defined as illustrated, or which may alternatively be more rounded and less defined. Thus, the bubble 50 in its original configuration has contoured sides 52 that correspond generally to the contours of the sides of the bristles 30, along edge 53 at the intersection of the top and sides (see, e.g., FIGS. 1 and 2). This shape is thought to provide a combination of aesthetic appeal as well as good functional performance in terms of e.g., ability to return to its original shape after being collapsed into the bristles and palpated.

The flexible portion 50 preferably has a least a portion made of a first material that is softer, more flexible, and/or more resilient than a second material that is used for other portions of the package. For example, in some embodiments, the flexible portion 50 may be made of a first material while the rest of the front cover 40 may be made of a second material that is more rigid than the first material. In some embodiments, the entire front cover 40 may be made from the first material.

The package 11 also includes the back cover 60, which may be a paperboard backer card. The package 11 may further include a wrap-around assembly 65, which may be formed integrally with the back card from a single, unitary section of card stock, and which extends from the back cover 60 to wrap around a portion of the front cover. The wrap-around assembly comprises top and bottom tabs 66a, 66b, each having a U-shaped slot 67a, 67b through which portions of the toothbrush handle 20 and front cover 40 extend. Each of the tabs 67a, 67b has a pair of flaps 69a-d that are tucked into side walls 68a, 68c when the package 11 is assembled to add strength and rigidity. The assembly 65 further comprises planar or substantially planar side walls 68a, 68c and a planar or substantially planar from wall 68b, all of which can be used to display product information, marketing information, instructions, and/or other relevant information. These walls also can be used generally to improve the appearance of the packaged implement by adding attractive shapes and colors to its appearance. In addition, the wrap-around assembly 65 can help to protect the head 27 of the toothbrush 20 from stacking loads or other loads that may be encountered during shipping handling and retail display.

To retain the wrap-around assembly 65 in a strong, rigid box-shaped configuration, the flaps 69a-d may be glued or otherwise joined to interior surfaces of the side walls 68a, 68c, and an additional flap or tab (not shown) may extend from the free edge of side wall 68c around the back of the back cover 60 so as to be joined thereto by a pressure-sensitive adhesive, hot melt glue, adhesive tape, stapling, welding, or other means. Alternatively, the assembly 65 may be held in place by a transparent plastic overwrap, a sleeve of shrink-wrap material, transparent tape, or other suitable means without an additional flap.

While the side walls 68a, 68c and front wall 68b of the embodiment of FIGS. 1-2 are rectangular, in other embodiments these structures may have other shapes, e.g., trapezoidal shapes. Also, while the illustrated wrap-around assembly 65 covers a portion of the handle above its lower or proximal end, leaving the lower end of the handle visible, the wrap-around assembly 65 in other embodiments may cover the lower end of the handle. Also, the wrap-around assembly 65 may in some cases comprise a single curved wall of e.g., semicircular or semi-elliptical cross-section, rather than having substantially planar front and side walls. In some embodiments, additional structure may be included outside of the front cover 40 that covers one or more portions of the neck of the toothbrush 20 and provides further strength and rigidity, as well as additional surfaces for inclusion of marketing information or other purposes.

In addition to the flexible region 50, the package 11 may include additional regions to permit users to feel various portions of the oral care implement. Portions of particular interest may include the soft tissue cleaner 23, and various portions of the handle 21 such as the grip zones 24, 25, the protruding ribs 26, or the handle 21 in its entirety to allow users to be more familiar with the ergonomic characteristics of the handle. In these embodiments, the corresponding portions of the package 11 may be constructed of the same material used in the construction of the flexible region 50.

Figure 4:
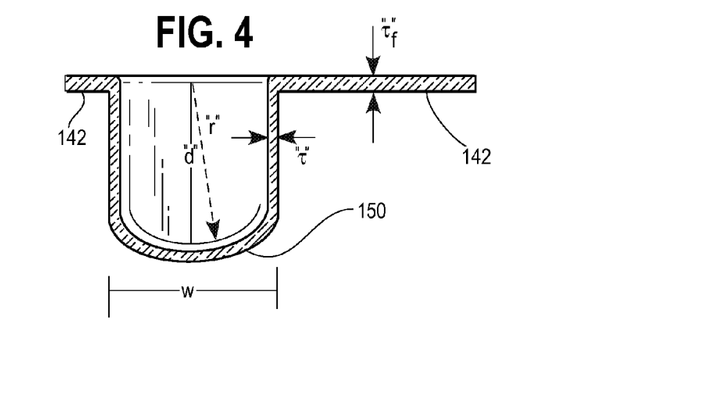
FIG. 4 is a cross sectional view along lines 4-4 in FIG. 3.

FIGS. 3-4 illustrate another embodiment in which an oral care implement is contained in a display package. The display package as shown is a "double-blister package" comprising a transparent front cover 140 and a transparent back cover 160 that are thermoformed or otherwise molded to define three-dimensional cavities. In the embodiment as shown, the back cover cavity 146 corresponds generally to the shape of the toothbrush, and includes a region of increased depth 162 for receiving the back of the head of the toothbrush.

In the embodiment of FIG. 3, the front cover 140 includes a rectangular-trapezoidal cavity 144 to accommodate a correspondingly shaped insert 145. Insert 145 may comprise side panels 145b and 145c on either side of a front panel 145a. Panels 145a, 145b, 145c may be used to display graphics, or to include product information, marketing information, instructions, and/or other relevant information. These surfaces also can be used generally to improve the appearance of the packaged implement by adding, attractive shapes and colors to its appearance. The insert 145 further comprises top and bottom tabs 148a, 148b, each having shaped slot 149a, 149b through which a portion of the toothbrush handle 20 extends.

The front cover 140 also includes a generally rectangular bubble portion 150, which may comprise a straight-sided protrusion having a somewhat square distal end 152, and a rounded and tapered proximal end 151. As shown in FIG. 4, the flexible bubble region 150 may have a generally outwardly convex front wall 153. In the embodiment of FIG. 4, the bubble has a depth "d" of between about ½ in. and 2 in., a width "w" of about ½ in. to 2½ in.; and a wall thickness "$\tau$" of between about 10 and 30 mils. The illustrated front wall 153 has a central region that has a radius of curvature "r," but in other embodiments the front wall 153 may not have a radius of curvature. Furthermore, rather than being outwardly convex, the front wall 153 may be flat, concave, or otherwise shaped. The flange region 142 has a thickness "$\tau_f$" that is preferably greater than that in the bubble portion 150. The thickness of the material of the bubble portion 150 may vary over its surface area.

The flexible region 150 may be any suitable shape or size, including but not limited to generally spherical, ellipsoidal, trapezoidal or rectangular. The properties of the flexible region 150 will depend on various factors including, the type of material selected, the thickness of the material, the shape of the flexible region 150, the distance the flexible region 150 is deflected, volume of the space deflected, and material properties such as the modulus of elasticity. The properties of the flexible region 150 can be selected to provide the consumer with the desired level of flexibility for a particular region of the product contained within the package. For example, the flexible region 150 for a user to engage with the bristles may have different characteristics than a flexible region for a user to engage with the grip pads.

A soft tissue cleanser such as a tongue and cheek cleanser 23 on the back of the toothbrush may be received in the protruding portion 162 of the back cover 160. The protruding region 162 may be made of a soft flexible material to allow the user deflect the protruding region 162 into contact with the tongue and cheek cleanser 23 to palpate the tongue and cheek cleaner 23 and obtain a tactile impression of its softness and resilience.

The package optionally further comprises an insert card 165 disposed between the flanges of the front cover 140 and the back cover 160 and extending about the perimeter of the package to provide an additional graphics display area. The insert card 165 may have instructions, logos, advertisements, and/or other marketing information printed thereon. All or a portion of the insert card 165 can be opaque so that product information can be effected conveyed to the consumer. The insert card 165 has a cut out region 165a which provides an opening through which the toothbrush 20 can be disposed between the front and back covers. The illustrated insert card 165 is flat, but in other embodiments the insert card may conform to interior cavity contours, or otherwise have a three-dimensional configuration. The insert card 165 may be a single layer or a multi-layer laminate of plastic, film, paperboard, metal foil, combinations thereof, or other suitable materials. The insert card 165 may be flexible or rigid.

The package may also include a tab 163 extending from the back cover 160. As illustrated in FIG. 3, the tab 163 is configured to fit within the distal end 152 of the protrusion 150 and to extend along one wall of the protrusion 150 to provide structural support and to transmit stacking loads from the back cover 160 of one package to the back cover of at package positioned immediately below it in a stack, or in the case of the package at the bottom of the stack, to a surface on which the stack is supported. For example, packaged oral care implements may be stacked on top of one another during shipping, handling and/or storage in a horizontal configuration e.g., with a package at the bottom of a stack having its front all lying on a support surface, and with the front wall of each package above it overlying the back wall of a package below it. The inclusion of tab 163 may help to avoid uneven stacking, and to avoid deformation of the bubble regions 150 which might lead to deformation of portions the oral care implement during shipping and handling. The tab 163 may also help to prevent the flexible bubble region 150 from being subjected to excessive compressive loads, thereby limiting deflection of the bubble 150 in response to stacking loads, or other static or dynamic loads, other than user-initiated pressure for purposes of bristle palpation. In some embodiments, the flexible region 150 can protrude to the same extent as any other extension from the front cover, such as the rectangular, trapezoidal configuration 144 of FIG. 3, to facilitate stacking, with supports 164 also bearing stacking loads and/or other loads on the lower handle 21 region of the packaging.

In some embodiments, one or more of the front cover 140, the back cover 160, and the bubble region 150 may be formed of the same flexible material. In such embodiments, the package may include structural elements that function similarly to the tab 163. These structural elements may be positioned within the package so as to provide rigidity and help to prevent the flexible portions of the package from being subjected to excessive compressive loads. In addition, the structural elements may help to define an area of the package where printed information may be attached to the package.

In certain embodiments, the display package may be formed by using both thermoforming and injection molding technologies. The display package may include blister covers that are made using a typical thermoforming process, with a subsequent cut in an upper portion of the package to create an opening. The bubble region 150 is subsequently molded over the blister to create a flexible bubble portion designed to provide tactile feel and recoverable shape to preserve the package and the product from destruction.

In an alternative embodiment, the display package may comprise a front cover and a back cover that are made from different materials. For example, the front cover may be made from paper substrate and the back cover may be a rigid or semi-rigid cover. In some embodiments, the front cover may include an opening where a bubble cover is disposed. The bubble cover is made from a softer material so as to provide the consumer with the desired level of flexibility for a particular region of the product contained within the package. The bubble cover may be made of the same material as the bubble region 150. In one embodiment, a toothbrush is disposed within the package with the entirety of the toothbrush located behind the front cover and the bead portion of the toothbrush located in the opening such that the tooth cleaning elements extend through the opening. In this embodiment, the consumer may engage the tooth cleaning elements via the bubble cover.

FIG. 5 illustrates a package for a toothbrush comprising a molded front cover 240 and a back cover 260 made from a thin flexible film. The front cover includes a cavity 246 that includes a bubble or protruding region 250 made of a first material such as TPU which is flexible and resilient, with surrounding portions being made of a second material which is not as flexible and resilient. The bubble 250 facilitates palpation of cleaning elements such as bristles on the head by the consumer. Additional flexible regions can be incorporated to provide for palpation of other portions of the implement by the consumer. The flexible regions may be distinct and separate, or they may be contiguous. Although the bubble 250 is depicted as a separate component from the front cover 240, it is understood that in some embodiments the bubble 250 may be formed integrally with the front cover 240 via a two-step injection molding process, for example. In some embodiments, the bubble 250 may be a separate component from the rest of the package. For example, in one embodiment, the front cover 240 may be made from a card hoard material, and the bubble 250 may be made separately and attached to the front cover 240 via any appropriate attachment means, such as via adhesive or the like.

As described above, the first material may be any suitable material having sufficiently soft, flexible, and resilient characteristics can be used for construction of the bubble region 250, such as TPU, silicone, synthetic and natural rubbers, elastomers, and monolayer or multilayer films including one or more layers of materials such as polyvinyl alcohol, polymethylmethacrylate, polyamide, polycarbonate, polyethylene, polypropylene, polyvinyl chloride, polystyrene, or combinations thereof.

The second material may be one that provides rigidity to the front cover. The second material may be, e.g., polyvinyl alcohol, polystyrene, polymethylmethacrylate, polycarbonate, PVC, PET/PETG or any other suitable material.

The flexible region 250 can be configured to allow deflection in any direction, or to allow deflection only in certain directions. For example, the flexible region can be deformable in a direction toward the back cover and/or in a direction parallel to the plane of the back cover. Deflection of the flexible region(s) can also be bi-directional, such that a pinching motion may be used to feel the softness of the bristles. Deflection of the flexible region can also be at an angle to the plane of the back cover. In the embodiment of FIG. 5, the bubble or protruding region 250 is made entirely of the first material, i.e., the flexible material. In some other embodiments, only a portion of the bubble region 250 is made of the first material.

The back cover 260 can be made of OPP, polyvinyl alcohol, polystyrene, polycarbonate, polymethylmethacrylate, PVC, PET/PETG or any other suitable material. In the embodiment of FIG. 5, the back cover 260 is made from peel-off lidding stock. The back cover can include a peel-off tab 261 which assists the user in peeling off the back cover. The front cover can be sealed to the back cover by a thermal weld, adhesive, interference fit, tap, tape, combinations thereof, or other suitable technique.

The package further includes upper and lower stacking lugs 248 and 247 that help to enable the packages to be arranged in stacks, wherein the ends 248a and 247a of the lugs abut the back cover of an adjacent package to bear stacking loads without imposing stacking loads on the bubbles 250 in excess of the bubbles' limited capacity to bear such loads. The lugs may be configured to cooperate with adjacent packages in a manner that enables a stack of 3 or more packages to snap together as a brick, enabling a reduction in packaging material associated with shipping cartons for the packed implements. The upper stacking lug 248 is generally U-shaped so as to define a slot that opens downward and to one side so as to function as a display hook, receiving and engaging a display rod, rack or the like in a retail setting to support the package, in addition to functioning as a stacking lug.

The front covers 240 may be formed by a two-shot injection molding process in which a first material such as rigid thin-walled polystyrene (OPS) is used to provide a rigid overall structure, and a second material such as a clear TPU soft material is used to provide a bubble. Spots of TPU may also be added to grip brush handles at 3 contact points or regions, e.g., a region at the proximal end 801, a region 802 between the proximal end 801 and grip pad 804, and a region 803 on the neck adjacent the head. It is understood that additional or less spots of TPU may be added to the package depending on the application. In addition, it is understood that in some embodiments, the spots of TPU may not be included in the regions described above.

Figure 6:
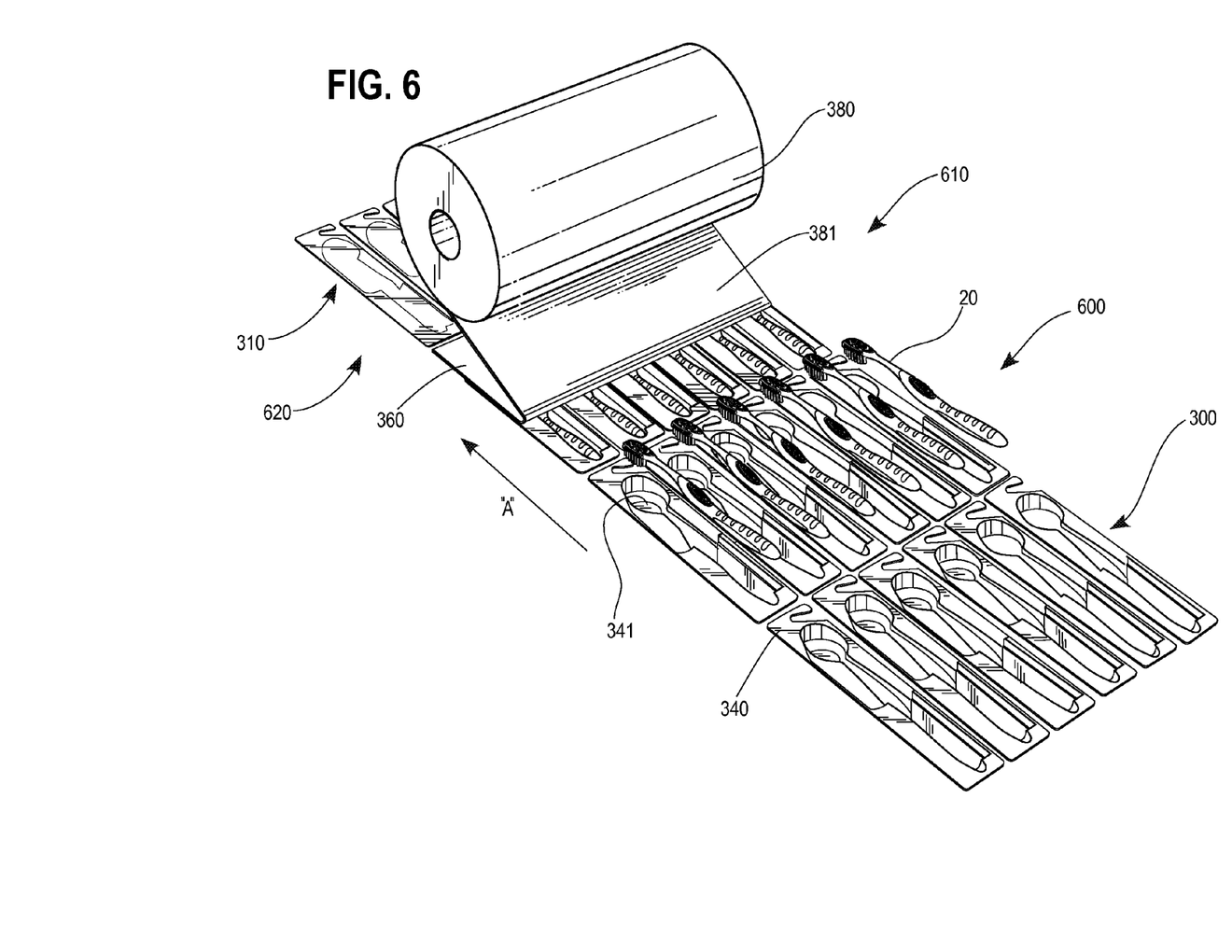
FIG. 6 is a perspective view illustrating assembly of the third embodiment.

FIG. 6 illustrates a method for forming the packages of FIG. 5. A conveying system, such as a conveyor belt, can be used to move the molded front covers 340 along various stations along the assembly pathway. A row 300 of molded front covers is conveyed from the molding station to a filling station 600. The molded covers may be formed in-line or at a remote location, and may be molded in nestable "trays" comprising, e.g., six covers arranged side-by-side. An oral care implement 20 is deposited robotically or manually into the cavity 341 of each of the molded front covers 340 at the filling station 600 and gripped by the spots of soft material at three locations. The filled molded front covers 340 are conveyed in a downstream direction "A" towards a sealing station 610 where the back cover 360 is applied to the back of the open mold cavity 341 to seal the oral care implement within the front and back covers 340,360. The back cover 360 is applied as a web of lidding stock 381 that is drawn from a supply source such as a roll 380 of lidding stock. The lidding may be heat sealed to the front covers 340, then die cut to form an easy-open flap that can be readily removed after purchase to access the toothbrush. Once the back cover has been applied to the row 300 of front covers, the packaged toothbrushes are further conveyed downstream to a separating station 620 wherein the packages are separated from one another to produce individual packaged oral care implements 310.

From the foregoing, it should be appreciated that the packaged oral care implement described herein provides significant advantages in the field of packaging such implements. While each of the packages in the three embodiments described in detail above comprises a front cover and a back cover that are joined to one another, packaging in accordance with other embodiments of the invention may have other configurations, e.g., configurations wherein the front and back comprise an integral, single, one-piece unitary structure, or wherein the packaging comprises a pair of generally tubular top and bottom covers.

Specifically, a toothbrush typically includes a head with cleaning elements such as bristles arranged in tufts. The bristle tufts may be arranged in various shapes, sizes and patterns. In addition to the bristle tufts, other elements such as thermoplastic elastomer (TPE) elements may also be provided to promote cleaning efficiency. A differentiating feature among toothbrushes is bristle stiffness. Although toothbrush packaging often includes an indication of bristle stiffness using a term such as "extra soft," "soft," "medium" or "hard," consumers sometimes wish to palpate and deflect the bristles prior to purchase, to feel the stiffness of the bristles. This may be due in part to some consumer experiences with low quality counterfeit or knockoff toothbrushes that are sometimes marketed in packaging, similar or identical to genuine articles. These low quality toothbrushes may have bristles that are of different stiffness than bristles on higher quality toothbrushes. The ends of the bristles in the low quality toothbrushes may also have less desirable characteristics. Rather than having, rounded ends or other end treatments, the bristles in low quality toothbrushes may have rough cut ends which may cause discomfort to the user during brushing, particularly if the bristles have a higher than desired degree of stiffness.

In some embodiments, to enable consumers to feel the bristles of a toothbrush, the soft flexible region comprises a bubble that has an original shape in which it is in close proximity to, or in contact with, the bristles of a toothbrush. The bubble region preferably is soft and flexible enough to enable consumers to feel differences in stiffness between bristles, such as those classified as "extra soft," "soft," "medium" or "hard" by palpating, the bristles through the bubble material, while also being resilient enough to return to its original configuration without detriment to its appearance after being release.

In order to palpate the head of a packaged toothbrush and assess bristle stiffness, consumers may apply pressure to the front cover with fingers or thumbs. This may cause localized buckling and distortion of the front cover, which can make the packaged toothbrush unsuitable for continued display, and thus may render the item unsaleable. Furthermore, the consumer may be unsatisfied with the tactile feedback obtained by attempting to assess bristle stiffness in this manner, because the consumer may be unable to feel a significant difference between bristles of varying stiffness across different toothbrushes, due to the stiffness and interference of the packaging material.

As described, the packaged oral care implement comprises a display package that is capable of protecting the oral care implement during shipping, handling and retail display, while also providing a soft, flexible region that facilitates improved tactile engagement of portions of the oral care implement by the consumer. Thus, the package enables the consumer to obtain more information, in the form of tactile feedback, so that the consumer can obtain information about not only the functionality and the "look," but also the "feel" of one or more portions of the implement.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. A package comprising:
   an oral care implement disposed in the package, the oral care implement including a head and a handle;
   a front cover comprising a flexible bubble and a handle portion, wherein the flexible bubble encloses the head of the oral care implement and the handle portion encloses the entire handle of the oral care implement;
   a back cover connected to the front cover; and
   wherein the flexible bubble is located proximate the head and is formed of a first material, and wherein the flexible bubble is sufficiently flexible and resilient such that the flexible bubble is capable of being deflected to allow a consumer to engage with the head of the oral care implement without permanent deformation of the flexible bubble, and
   wherein the handle portion is formed of a second material, the first material comprising a different material from the second material, and wherein the handle portion is more rigid than the flexible bubble.

2. The package of claim 1 wherein a wall thickness of the front cover is less than a wall thickness of the flexible bubble.

3. The package of claim 2 wherein the flexible bubble and the front cover are formed separately.

4. The package of claim 2 wherein the flexible bubble and the front cover are formed integrally.

5. The package of claim 1 wherein at least a portion of the flexible bubble extends at a distance from an outer surface of the front cover in a direction away from the back cover.

6. The package of claim 1 wherein the flexible bubble comprises TPU.

7. The package of claim 1 wherein the front cover comprises polystyrene.

8. The package of claim 1 wherein the oral care implement comprises a toothbrush.

9. A packaged oral care implement comprising:
an oral care implement having a plurality of tooth engaging elements and a handle; and
a blister package, comprising:
a front cover comprising a flexible bubble which encloses the tooth engaging elements and a handle portion which encloses the entire handle of the oral care implement,
a back cover connected to the front cover to enclose the oral care implement, and
wherein the flexible bubble is made of a first material and the handle portion of the front cover is made of a second material that is different from the first material and wherein a wall thickness of the front cover is greater than a wall thickness of the flexible bubble, such that the handle portion of the front cover is more rigid than the flexible bubble, and
wherein the blister package further comprises a structural element configured to provide structural support and to transmit a stacking load to protect the flexible bubble from deformation.

10. The packaged oral care implement of claim 9 wherein the structural element is an extension of the back cover.

11. The packaged oral care implement of claim 9 wherein the flexible bubble allows contact with the tooth engaging elements without permanent deformation of the blister package and the flexible bubble is capable of reverting to the original configuration after multiple deflections.

12. The packaged oral care implement of claim 9 wherein the flexible bubble comprises TPU and the front cover comprises polystyrene.

13. A packaged oral care implement comprising:
an oral care implement having at least one flexible element and a handle, the at least one flexible element comprising a plurality of bristles; and
a package enclosing the oral care implement;
the package including at least one rigid region and a flexible region, said flexible region enclosing the at least one flexible element of the oral care implement, said rigid region enclosing the entire handle;
wherein a wall thickness of the at least one rigid region adjacent the flexible region is greater than a wall thickness of the flexible region, and wherein the flexible region is made of a first material and the at least one rigid region is made of a second material that is different from the first material,
the flexible region having a first modulus of elasticity $(\lambda_1)$, and the at least one rigid region having a second modulus of elasticity $(\lambda_2)$, wherein $(\lambda_1)/(\lambda_2)<1$.

14. The packaged oral care implement of claim 13 wherein the oral care implement is a toothbrush, and wherein the flexible region comprises a bubble that has an original configuration where the bubble and the at least one flexible element are undeflected.

15. The packaged oral care implement of claim 14 wherein the package comprises a front cover and a back cover, and wherein the flexible region is on the front cover and is capable of reverting to the original configuration after multiple deflections.

16. The packaged oral care implement of claim 15 wherein the back cover comprises a backer card.

17. The packaged oral care implement of claim 15 wherein the back cover comprises a plastic blister.

18. The packaged oral care implement of claim 15 wherein the back cover is made of a non-molded flexible film material.

* * * * *